US008067357B2

(12) United States Patent
Reutelingsperger et al.

(10) Patent No.: US 8,067,357 B2
(45) Date of Patent: Nov. 29, 2011

(54) ANNEXIN DERIVATIVES SUITABLE FOR PRETARGETING IN THERAPY AND DIAGNOSIS

(75) Inventors: Christiaan Peter Maria Reutelingsperger, Maastricht (NL); Peter Moonen, Susteren (NL); Ad Vermaire, Kattendijke (NL)

(73) Assignee: Mosamedix B.V., Kattendijke (NL)

( * ) Notice: Subject to any disclaimer, the term of this patent is extended or adjusted under 35 U.S.C. 154(b) by 439 days.

(21) Appl. No.: 12/096,996

(22) PCT Filed: Dec. 12, 2006

(86) PCT No.: PCT/NL2006/050315
§ 371 (c)(1),
(2), (4) Date: Oct. 20, 2008

(87) PCT Pub. No.: WO2007/069895
PCT Pub. Date: Jun. 21, 2007

(65) Prior Publication Data
US 2009/0155170 A1 Jun. 18, 2009

(30) Foreign Application Priority Data

Dec. 12, 2005 (EP) .................................... 05111982

(51) Int. Cl.
*C07K 14/00* (2006.01)
(52) U.S. Cl. .......................................... 514/1; 530/350
(58) Field of Classification Search .................. 530/350; 514/1
See application file for complete search history.

(56) References Cited

U.S. PATENT DOCUMENTS 7,511,016 B2 * 3/2009 Reutelingsperger ........... 514/1.1
2006/0024315 A1 * 2/2006 Schnitzer et al. ......... 424/155.1

FOREIGN PATENT DOCUMENTS
WO WO 2006/003488 A2 1/2006

OTHER PUBLICATIONS

Clemen et al. 2001; Annexin VII; an astroglial protein exhibiting a Ca2+-dependent subcellular distribution. NeuroReport 12(6): 1139-1144.*
Mira, et al., "Inhibition of Cytosolic Phospholipase A2 by Annex in V in Differentiated Permeabilized HL-60 Cells. Evidence of Crucial Importance of Domain I Type II Ca2+-Binding Site in the Mechanism of Inhibition," *Journal of Biological Chemistry*, Apr. 18, 1997, vol. 272, No. 16, pp. 10474-10482.
Kenis, et al., "Cell Surface-Expressed Phosphatidylserine and Annexin A5 Open a Novel Portal of Cell Entry," *Journal of Biological Chemistry*, Dec. 10, 2004, vol. 279, No. 50, pp. 52623-52629.
Huber, et al., "The Crystal and Molecular Structure of Human Annexin V, an Anticoagulant Protein that Binds to Calcium and Membranes," *Embo Journal*, Dec. 1990, pp. 3867-3874.

* cited by examiner

*Primary Examiner* — Karen Carlson
(74) *Attorney, Agent, or Firm* — Gilberto M. Villacorta; Sunit Talapatra; Foley & Lardner LLP

(57) ABSTRACT

The present invention provides methods and compositions for the treatment and diagnosis of diseases such as neoplastic diseases, neurodegenerative diseases, cardiovascular diseases, autoimmune diseases, and inflammatory diseases. The methods are based on the concept of pretargeting and include the administration of complexes comprising a recognizable compound A coupled to annexins, and the administration of complexes comprising of pharmaceutical or diagnostic compounds coupled to a compound B recognizing and binding to compound A to subjects. The compositions include annexins, annexin variants, that are not internalized by the target cells, derivatives thereof, and complexes thereof.

15 Claims, 3 Drawing Sheets

Figure 1. SEQ ID NO: 1

| | | | | |
|---|---|---|---|---|
| *AQVLRGTVTD* | *FPGFD*ERADA | ETLRKAMKGL | GTDEESILTL | 40 |
| LTSRS*NAQRQ* | *EISAAFKT*LF | GRDLLDDLKS | ELTGKFEKLI | 80 |
| VALMK*PS*RLY | DAYELKHALK | GAGTNEKVLT | EIIASRT*PEE* | 120 |
| *LRAIKQVYEE* | *EYGS*SLEDDV | VGDTSGYYQR | MLVVLL*QANR* | 160 |
| *DPDAGIDEAQ* | VEQDAQALFQ | AGELKWGTDE | EKFITIFGTR | 200 |
| SV*SHLRKVFD* | *KYMTISGFQI* | EETIDRETSG | NLEQLLLAVV | 240 |
| KSIR*SIPA*YL | AETLYYAMKG | AGTDDHTLIR | VMVSRSEID*L* | 280 |
| *FNIRKEFRKN* | *FATS*LYSMIK | GDTSGDYKKA | LLLLCGEDD | 319 |

Figure 2. ALIGNMENT OF SOME HUMAN ANNEXINS A1, A2, A3, A4 A5, A6, A7, A8, A9, A10, A11 and A13 (SEQ ID NOS 2-13, respectively in order of appearance):

```
 28 KGGPGSAVSPYPTFNPSSDVAALHKAIMVKGVDEATIIDILTKRNNAQRQQIKAAYLQET  A1
 19 PPSAYGSVKAYTNFDAERDALNIETAIKTKGVDEVTIVNILTNRSNAQRQDIAFAYQRRT  A2
  4 WVGHRGTVRDYPDFSPSVDAEAIQKAIRGIGTDEKMLISILTERSNAQRQLIVKEYQAAY  A3
  1   ATKGGTVKAASGFNAMEDAQTLRKAMKGLGTDEDAIISVLAYRNTAQRQEIRTAYKSTI  A4
  1 AQVLRGTVTDFPGFDERADAETLRKAMKGLGTDEESILTLLTSRSNAQRQEISAAFKTLF  A5
350 RVELKGTVRPANDFNPDADAKALRKAMKGLGTDEDTIIDIITHRSNVQRQQIRQTFKSHF  A6
172 TQVTQGTIRPAANFDAIRDAEILRKAMKGFGTDEQAIVDVVANRSNDQRQKIKAAFKTSY  A7
  8 IEQEGVTVKSSSHFNPDPDAETLYKAMKGIGTNEQAIIDVLTKRSNTQRQQIAKSFKAQF  A8
 28 AWGTLGTLRTFLNFSVDKDAQRLLRAITGQGVDRSAIVDVLTNRSREQRQLISRNFQERT  A9
  4 GDYVQGTIFPAPNFNPIMDAQMLGGALQGFDCDKDMLINILTQRCNAQRMMIAEAYQSMY  A10
187 QFGSRGTITDAPGFDPLRDAEVLRKAMKGFGTDEQAIIDCLGSRSNKQRQQILLSFKTAY  A11
  1  GNRHAKASSPQGFDVDRDAKKLNKACKGMGTNEAAIIEILSGRTSDERQQIKQKYKATY  A13

88 GKPLDETLKKALTGHLEEVVLALLKTPAQFDADELRAAMKGLGTDEDTLIEILASRTNKE
 79 KKELASALKSALSGHLETVILGLLKTPAQYDASELKASMKGLGTDEDSLIEIICSRTNQE
 64 GKELKDDLKGDLSGHFEHLMVALVTPPAVFDAKQLKKSMKGAGTNEDALIEILTTRTSRQ
 60 GRDLIDDLKSELSGNFEQVIVGMMTPTVLYDVQELRRAMKGAGTDEGCLIEILASRTPEE
 61 GRDLLDDLKSELTGKFEKLIVALMKPSRLYDAYELKHALKGAGTNEKVLTEIIASRTPEE
410 GRDLMTDLKSEISGDLARLILGLMMPPAHYDAKQLKKAMEGAGTDEKALIEILATRTNAE
232 GKDLIKDLKSELSGNMEELILALFMPPTYYDAWSLRKAMQGAGTQERVLIEILCTRTNQE
 68 GKDLTETLKSELSGKFERLIVALMYPPYRYEAKELHDAMKGLGTKEGVIIEILASRTKNQ
 88 QQDLMKSLQAALSGNLERIVMALLQPTAQFDAQELRTALKASDSAVDVAIEILATRTPPQ
 64 GRDLIGDLREQLSDHFKDVMAGLMYPPPLYDAHELWHAMKGVGTDENCLIEILASRTNGE
247 GKDLIKDLKSELSGNFEKTILALMKTPVLFDIYEIKEAIKGVGTDEACLIEILASRSNEH
 60 GKELEEVLKSELSGNFEKTALALLDRPSEYAARQLQKAMKGLGTDESVLIEFLCTRTNKE

148 IRDINRVYREELKRDLAKDITSDTSGDFRNALLSLAKGDRSEDFGV         NEDLADSDARALYE
139 LQEINRVYKEMYKTDLEKDIISDTSGDFRKLMVALAKGRRAEDGSVI        DYELIDQDARDLYD
124 MKDISQAYYTVYKKSLGDDISSETSGDFRKALLTLADGRRDESLKV         DEHLAKQDAQILYK
120 IRRISQTYQQQYGRSLEDDIRSDTSFMQRVLVSLSAGGRDEGNYL          DDALVRQDAQDLYE
121 LRAIKQVYEEEYGSSLEDDVVGDTSGYYQRMLVVLLQANRDPDAGI         DEAQVEQDAQALFQ
470 IRAINEAYKEDYHKSLEDALSSDTSGHFRRILISLATGHREEGGENLDQAREDAQVAAEILEIAD
292 IREIVRCYQSEFGRDLEKDIRSDTSGHFERLLVSMCQGNRDENQSI         NHQMAQEDAQRLYQ
128 LREIMKAYEEDYGSSLEEDIQADTSGYLERILVCLLQGSRDDVSSFV        DPALALQDAQDLYA
148 LQECLAVYKHNFQVEAVDGITSETSGILQDLLLALAKGGRDSYSGII        DYNLAEQDVQALQR
124 IFQMREAYCLQYSNNLQEDIYSETSGHFRDTLMNLVQGTREEGYT          DPAMAAQDAMVLWE
307 IRELNRAYKAEFKKTLEEAIRSDTSGHFQRLLISLSQGNRDESTNV         DMSLAQRDAQELYA
120 IIAIKEAYQRLFDRSLESDVKGDTSGNLKKILVSLLQANRNEGDDV         DKDLAGQDAKDLYD

208 AGERRKGTDVNVFNTILTTRSYPQLRRVFQKYTKYSKHDMNKVLDLELKGDIEKCLTAIV  A1
200 AGVKRKGTDVPKWISIMTERSVPHLQKVFDRYKSYSPYDMLESIRKEVKGDLENAFLNLV  A2
184 AGENRWGTDEDKFTEILCLRSFPQLKLTFDEYRNISQKDIVDSIKGELSGHFEDLLLAIV  A3
180 AGEKKWGTDEVKFLTVLCSRNRNHLLHVFDEYKRISQKDIEQSIKSETSGSFEDALLAIV  A4
181 AGELKWGTDEEKFITIFGTRSVSHLRKVFDKYMTISGFQIEETIDRETSGNLEQLLLAVV  A5
535 TPSGDKTSLETRFMTILCTRTYPHLRRVFQEFIKMTNYDVEHTIKKEMSGDVRDAFVAIV  A6
352 AGEGRLGTDESCFNMILATRSFPQLRATMEAYSRMANRDLLSSVSREFSGYVESGLKTIL  A7
189 AGEKIRGTDEMKFITILCTRSATHLLRVFEEYEKIANKSIEDSIKSETHGSLEEAMLTVV  A8
209 A      EGPSREETWVPVFTQRNPEHLIRVFDQYQRSTGQELEEAVQNRFHGDAQVALLGLA A9
183 ACQQKTGEHKTMLQMILCNKSYQQLRLVFQEFQNISGQDMVDAINECYDGYFQELLVAIV  A10
367 AGENRLGTDESKFNAVLCSRSRAHLVAVFNEYQRMTGRDIEKSICREMSGDLEEGMLAVV  A11
180 AGEGRWGTDELAFNEVLAKRSYKQLRATFQAYQILIGKDIEEAIEEETSGDLQKAYLTLV  A13
```

Figure 2 (cont'd)

```
268 KCATSKPAFFAEKLHQAMKGVGTRHKALIRIMVSRSEIDMNDIKAFYQKMYGISLCQAIL
260 QCIQNKPLYFADRLYDSMKGKGTRDKVLIRIMVSRSEVDMLKIRSEFKRKYGKSLYYYIQ
244 NCVRNTPAFLAERLHRALKGIGTDEFTLNRIMVSRSEIDLLDIRTEFKKHYGYSLYSAIK
240 KCMRNKSAYFAEKLYKSMKGLGTDDNTLIRVMVSRAEIDMLDIRAHFKRLYGKSLYSFIK
241 KSIRSIPAYLAETLYYAMKGAGTDDHTLIRVMVSRSEIDLFNIRKEFRKNFATSLYSMIK
595 QSVKNKPLFFADKLYKSMKGAGTDEKTLTRIMVSRSEIDLLNIRREFIEKYDKSLHQAIE
412 QCALNRPAFFAERLYYAMKGAGTDDSTLVRIVVTRSEIDLVQIKQMFAQMYQKTLGTMIA
249 KCTQNLHSYFAERLYYAMKGAGTRDGTLIRNIVSRSEIDLNLIKCHFKKMYGKTLSSMIM
266 SVIKNTPLYFADKLHQALQETEPNYQVLIRILISRCETDLLSIRAEFRKKFGKSLYSSLQ
243 LCVRDKPAYFAYRLYSAIHDFGFHNKTVIRILIARSEIDLLTIRKRYKERYGKSLFHDIR
427 KCLKNTPAFFAERLNKAMRGAGTKDRTLIRIMVSRSETDLLDIRSEYKRMYGKSLYHDIS
240 RCAQDCEDYFAERLYKSMKGAGTDEETLIRIVVTRAEVDLQGIKAKFQEKYQKSLSDMVR

328 DETKGDYEKILVALCGGN       A1
320 QDTKGDYQKALLYLCGGDD      A2
304 SDTSGDYEITLLKICGGDD      A3
300 GDTSGDYRKVLLVLCGGDD      A4
301 GDTSGDYKKALLLLCGEDD      A5
655 GDTSGDFLKALLALCGGED      A6
472 GDTSGDYRRLLLAIVGQ        A7
309 EDTSGDYKNALLSLVGSDP      A8
326 DAVKGDCQSALLALCRAEDM     A9
303 NFASGHYKKALLAICAGDAEDY   A10
487 GDTSGDYKILLKICGGND       A11
300 SDTSGDFRKLLVALLH         A13
```

ANNEXIN DERIVATIVES SUITABLE FOR PRETARGETING IN THERAPY AND DIAGNOSIS

The present invention relates generally to the field of annexins. More particularly, it relates to compositions and methods for treating and diagnosing a subject by delivering compounds to a specified target using novel annexins, variants of annexins, and derivatives thereof that do not form trimers and 2-dimensional networks.

BACKGROUND OF THE INVENTION

Cells are enveloped by a plasma membrane ("PM") that consists of a bilayer of phospholipid molecules and several protein molecules. Various phospholipid molecules form the building blocks of the bilayer. The phospholipid molecules are distributed asymmetrically over the two leaflets of the bilayer. Phosphatidylcholine for example is present in both layers, whereas sphingomyeline can be found only in the outer leaflet facing the environment. Aminophospholipids, like phosphatidylserine ("PS"), on the other hand, are predominantly present in the inner leaflet facing the cell's cytosol (Zwaal and Schroit, Blood 89:1121-32 (1997)). Aminophospholipid translocases transport PS from the outer to the inner layer, or leaflet, of the plasma membrane to create an asymmetric distribution of PS. The asymmetric architecture of the PM is a feature of living cells. They expend energy to generate and maintain the uneven distribution of the phospholipid species in their PM's.

A cell can change the phospholipid architecture of its PM under certain circumstances, which lead to activation and perturbation of the cell. Programmed cell death ("PCD") is associated with the appearance of PS in the outer leaflet of the PM (Fadok et al., J. Immunol. 148:2207-16 (1992)). On the basis of morphology and biochemistry, at least four types of PCD have been identified: (1) apoptosis, (2) apoptosis-like PCD, (3) necrosis-like PCD, and necrosis. Each type is accompanied by a change in the asymmetry of the PM characterized by exposure of PS to the outer layer of the cell surface. PS exposure at the outer layer of the PM is a good indication of a variety of activated and perturbed states of a cell. PS exposure, however, is not exclusively associated with cellular processes culminating in cell death. Transient and reversible PS exposure has been reported for several cell types, including activated B cells, undifferentiated muscle cells prone to form syncytium, chlamydia infected cells, endothelial cells of tumour vasculature (U.S. Pat. No. 6,312,694), and engulfing macrophages (Kenis et al. J. Biol. Chem. 2004 279: 52623-9). In addition, several cellular processes and conditions have been found that are associated with an expression of PS at the outer leaflet of the PM. These include platelet activation, red blood cell ageing, stimulation of the immune system, muscle cell syncytium formation, new blood vessel formation in tumors (U.S. Pat. No. 6,312,694), and tumor growth (Rao et al., Thromb. Res. 67:517-31 (1992)).

In addition, cells can dissipate portions of themselves from their surface resulting in membrane encapsulated microparticles. These microparticles have aminophospholipids such as PS exposed at the outer layer of the membranes. These microparticles have been associated with diseases like infection, AIDS, atherosclerosis. Therefore, aminophospholipids at the cell surface are indicators of a variety of activated and perturbed states of a cell. Moreover, microparticles that exhibit exposed aminophospholipids reflect distant cell activation and perturbation. Hence, phospholipids at the surface of a PM constitute attractive targets for a variety of purposes including research, diagnosis, prevention and treatment of diseases. Preferably, PS in the outer leaflet of a PM constitutes a target for research, diagnosis, prevention and treatment of diseases.

Pharmacological and genetic treatments of diseases are based on the delivery of pharmacologically active compounds to diseased cells where the compounds act preferably intracellularly. Current therapeutic treatments employ systemic delivery of a drug, where the drug circulates through the entire body before reaching its desired target. This method of drug delivery results in systemic dilution of the compound. As a result higher concentrations of the drug are required to achieve a therapeutic efficacy. This is associated with undesired toxic side-effects and increased costs of drugs.

Solutions to these problems are provided by targeted drug delivery systems. The targeting agent, which is coupled to the drugs directly or indirectly, guides the drugs to the diseased cells where they accumulate.

Recently we described annexins, derivatives thereof and annexin-Cys variants as targeting and cell-entry agents and their uses for therapeutic and diagnostic applications (WO 2006/003488, published 12 Jan. 2006). The predominant target of annexins is phosphatidylserine (PS), which is exposed by cells that execute programmed cell death or are submitted to stress such as metabolic stress. The annexins, derivates and annexin-Cys variants as described in WO 2006/003488 bind to cell surface exposed PS and are subsequently internalized. The internalization results in a depletion of surface-bound annexins. This phenomenon disfavours the use of annexins in therapeutic and diagnostic procedures that employ the concept of pretargeting.

Pretargeting is a strategy of targeting a reporting compound for diagnostic purposes and/or a drug for therapeutic purposes to the diseased tissue in a multi-step procedure in order to reduce the background signal and the systemic toxic burden respectively. The pretargeting concept employs two compounds A and B which have a high affinity for each other. Compound A encompasses the targeting function and compound B contains the reporter and/or therapeutic function. Firstly, compound A with the targeting function is administered to the subject. After a certain period of time when the circulating compound A is cleared sufficiently, compound B with the reporter and/or therapeutic drug is given to the subject. The latter compound will accumulate at sites where compound A is retained due to its targeting function. This strategy reduces the amount of compound B that needs to be administered in order to obtain the desired effect. Moreover, it will circumvent background signals and undesired toxic side-effects that are related to compound A if the reporter and/or therapeutic drug were directly coupled to compound A.

Examples of combinations of A and B compounds that have high affinity for each other and that are suitable for pretargeting include the streptavidin/avidin and biotin combination, combination of complementary DNA and RNA oligonucleotides, complementary DNA and RNA analogs such as morpholinos (synthetic oligonucleotide analogues containing morpholino-phosphorodiimidate chains instead of deoxyribose-phosphodiester chains), peptide nucleic acids (synthetic oligonucleotide analogues containing N-aminoethyl-glycine chains instead of deoxyribose-phosphodiester chains, PNA) and aptamers (specifically binding oligonucleotides or oligopeptides), the antibody and hapten combination, and the receptor and ligand combination. These combinations have been used in delivery of radionuclides for imaging and therapy of cancer through the pretargeting strategy (Sharkey et al, Clin. Cancer Res. 2005, 11:7109-21).

The prerequisite for successful implementation of the pretargeting strategy is the accessibility of compound A for compound B. Internalization of compound A by the target cell would reduce the efficacy of this strategy.

Patent application WO 2006/003488, describes that annexins, derivatives thereof, and annexin-Cys variants are internalized by cells that expose PS at their surface. The mechanism of internalization is based on the formation of annexin-trimers and the organization of the annexin-trimers in large 2-dimensional networks (Kenis et al. *J. Biol. Chem.* 2004 279: 52623-9). This mechanism, thus, diminishes the efficient use of annexin, derivatives thereof, and annexin-Cys variants as targeting parts of compound A in pretargeting strategies.

Mira et al., *J. Biol. Chem.* 1997, 272: 10474-82, describe annexin mutants M1-M4, which affect $Ca^{2+}$ binding and the effect thereof on inhibition of cytosolic phospholipase $A_2$.

SUMMARY OF THE INVENTION

In accordance with one embodiment of the invention there is provided annexin variants that are suitable for pretargeting strategies for diagnosing and treating diseases. These annexin variants bind PS with sufficient affinity and are unable to form trimers and 2-dimensional networks on the cellular surface and, hence, they do not induce their own internalization.

Another embodiment of the invention concerns annexins and variants thereof that are derivatised with affinity compounds A for pretargeting strategies. Such affinity compounds include biotin, compounds containing one or more biotin groups, streptavidin, avidin, DNA oligonucleotides, RNA oligonucleotides, morpholinos, PNA's, aptamers, receptors, compounds with high affinity for receptors and immuno-globulins or parts thereof. In the present invention, affinity compound A is also referred to as recognizable compound (A), or as compound A, with the same meaning.

A further embodiment of the invention comprises annexins, derivatives thereof and annexin-Cys variants according to patent application WO 2006/003488 that are derivatised with affinity compounds A via conjugation to the cysteine residue.

One embodiment of the invention relates to the use of affinity compounds B that are conjugated with fluorescent compounds, radionuclides, MRI contrast agents, CT contrast agents, cytostatics, and therapeutic biologicals including cytokines, complement factors, toxins, and immunoglobulins in combination with the annexin derivatives and complexes. Affinity compounds B have a high affinity for affinity compounds A of other embodiments of the invention. In the present invention, affinity compound B is also referred to as compound (B) recognizing compound A, or as recognizing compound B, or compound B, with the same meaning.

One embodiment of the present invention is a kit that includes at least one complex of annexin derivative with affinity compound A described above and, optionally at least one pharmaceutically acceptable excipient.

Another embodiment of the invention relates to a method for delivering a pharmaceutical compound to a target cell that includes administering firstly a targeting complex of the composition that is described above and secondly a therapeutic complex of the composition that is described above. More specifically, this embodiment encompasses a method to treat or prevent a disease, where the pharmaceutical compound is a therapeutic compound that is effective to treat or prevent the disease.

One embodiment of the invention relates to a method for delivering a diagnostic compound to a target cell that includes administering firstly a targeting complex of the composition that is described above and secondly a diagnostic complex of the composition that is described above. More specifically this embodiment encompasses a method to diagnose a disease and to determine the efficacy of a therapeutic treatment, where the diagnostic compound is a molecular imaging compound that can be detected by imaging modalities comprising optical imaging, nuclear imaging, MRI, CT and ultrasound.

For a better understanding of the present invention, together with other and further objects thereof, reference is made to the following description, taken in conjunction with the accompanying drawings, and its scope will be pointed out in the appending claims.

DETAILED DESCRIPTION OF THE INVENTION

The present invention is based in part on the directed search to identify those amino acids that are involved in the intermolecular interactions between annexin molecules. Molecular modelling and docking of the crystal structures available in the Protein Database (PDB, 1AVR and ANX) revealed amino acids that are involved in the trimer formation. These amino acids are found in the helices IA, ID, IIA, IID, IIIC, IIID and IVE and in the stretches connecting helices IC and ID, IIE and IIIA, IIIC and IIID, IIID and IIIE, and IVA and IVB (for localization of these helices in the annexin A5 molecule see Huber et al. *EMBO J* 12:3867-74 (1990)). The annexin variants of one of the embodiments of the invention have one or more amino acids replaced in the helices IA, ID, IIA, IID, IIIC, IIID and IVE and in the stretches connecting helices IC and ID, IIE and IIIA, IIIC and IIID, IIID and IIIE, and IVA and IVB so as to impair their ability to form trimers and a 2-dimensional network on the cellular surface and consequently to impair their internalization into the cell. The annexin variants will remain longer on the cellular surface and are, thus, suitable for pretargeting strategies.

Thus, the invention generally pertains to an annexin variant, a) that binds to at least one phospholipid, in particular to phosphatidylserine (PS), and b) that is not internalized into a cell. The term "annexin" refers to any protein capable of binding to phospholipids, especially phosphatidylserine, and member of the so-called annexin family. The family covers many members; information thereon and on the protein and nucleotide sequences can for example be found on http://snoops.bch.ed.ac.uk/annexins/seq/-search.php. By way of example, reference is made herein to annexin A5, having the amino acid sequence of SEQ ID No. 1, but other annexins can equally be used for producing and using the annexin variants of the invention. FIG. 2 contains an alignment of human annexins A1 to A11 and A13. Some of the annexins, such as A1, A6, A7 and A11 have long extensions at the N-terminus. These parts have not been included in FIG. 2, and are believed to be less relevant for the purpose of the invention. Here below, reference is made to the amino acid sequence and the positions of annexin A5, but what applies to A5 also applies to the other annexins, especially human annexins, by choosing the corresponding position found with the alignment of FIG. 2 or corresponding alignment of any annexins not represented in FIG. 2.

Specific annexin variants according to the invention have amino acid sequences according to FIG. 1 (SEQ ID NO: 1), which are modified to inhibit the internalization into a cell in that one or more amino acids within the helices and connecting stretches indicated above are replaced by different amino acids. These amino acids are located at positions 16-29, 59-74, 88-102, 135-145, 156-169, 202-231, 259-266, and 305-317 in annexin A5, and these positions are underlined in SEQ ID No. 1 and in FIG. 2. Where the annexin variant contains one or more of these modifications, the feature of the annexin not being internalized into a cell is considered as being fulfilled. Thus, the invention also comprises an annexin variant that a) binds to at least one phospholipids and b) contains one or more of the amino acid modifications as described herein.

Preferred modifications are substitutions, especially substitutions of polar amino acids by non-polar amino acids. Thus, preferred amino acids for substitution include arginine (R), lysine (K), aspartate (D), glutamate (E), asparagine (N) and glutamine (Q). They may be substituted e.g. by alanine (A) or glycine (G), or by a non-polar amino acid that is located in the corresponding position of another annexin (cf. FIG. 2). Suitable examples of substituted amino acids include E21, K25 (e.g. by G, T), R62 (e.g. G, A), D63 (e.g. G, A, P), K69, D91, K96, H97, K100, E137 (e.g. A, G, V), D138, D139, N159 (e.g. A, G, S), R160, R206, K207, Q219, D225, R226, D264, K308, K309. The modifications M1-M4, at positions E71, D143, E227 and D302, are less preferred according to the invention.

It is preferred to have at least two, or even at least three, substitutions in different regions, for example R62A+E137G, or K69A+K100A+N159S etc., in order to further decrease the trimerisation of the annexin at the site of the cell.

The annexin variants according may further comprise one or more amino acid substitutions, deletions, or additions, wherein the amino acid substitutions, deletions, or additions do not substantially affect the ability of the annexin variant to bind to at least one phospholipid, and to bind at least on recognizable compound A, and wherein the amino acid substitutions, deletions, or additions do not substantially affect the inhibited internalization of the recognizable compound A into a cell.

The substitution must be such that the annexin still binds sufficiently to the phospholipid. Sufficient binding means a dissociation constant of approximately $10^{-6}$ M or less in the presence of $Ca^{2+}$-ions.

The invention further pertains to annexin molecules or variants as defined above to which a recognizable compound A, wherein the annexin variant is not internalized by the target cell. The recognizable compound A may for example be a biotin or a complex of multiple biotins. Other suitable examples include avidin or streptavidin, an oligonucleotide or a nuclease-resistant oligonucleotide analogue in the form of a morpholino compound or a PNA or an aptamer.

In another embodiment the recognizable compound A is a receptor or a part thereof, or a receptor ligand or a part thereof. Other examples of recognizable compounds A include an antibody or a fragment thereof, for example a nanobody—a truncated antibody from camel-like origin—, or an antigen.

The recognizable compound can be bound to the annexin by methods known per se. One method consists in covalently binding the recognizable compound to specific amino acids, possibly in derivatised form. Especially suitable is binding to a cysteine residue of the annexin, for example in the case of biotin, which can be derivatised with a maleimide group. In order not to interfere with functional properties of the annexin, the amino acid to which the recognizable compound is coupled is located at the concave sides of the annexin molecule. These are represented by italic amino acid symbols in SEQ ID NO. 1. Moreover, these positions may or may not be located in the regions selected above for preventing trimerisation and internalization of the annexin. Thus the preferred sites are the bold italic positions in SEQ ID No. 1, i.e. the stretches 1-15, 46-58, 86-87, 118-134, (170), 245-248 and 280-294 of annexin A5 and the corresponding stretches in other annexins (see FIG. 2), but underlined italic positions (16-19, 24, 28, 59-64, 88-89, 135, 157-169, 203-219) can also be used for introducing cysteine residues.

It is furthermore preferred that any cysteine residues naturally present outside these stretches, especially those which are present in the parts where amino acids are substituted according to the invention for the purpose of preventing trimerisation, are replaced by other amino acids. Such other amino acid can be a neutral small amino acid such as G, A or S, or an amino acid that is present at the same position ion of another annexin. For example, C107 of annexin A4 can suitably be replaced by V or A, C201 of annexin A3 (and the counterparts in many other annexins) can be replaced by G or A, and C315 in annexin A5 (and the counterparts in many other annexins) can be replaced by V, A or S. The C292 of annexin A8 need not be replaced as it is in a position suitable for derivatisation. The amino acid substitutions can be performed by recombinant techniques well-known in the art and illustrated in the examples below.

Thus the invention pertains to an annexin variant, which contains a cysteine residue at one of the amino acid positions 1-19, 24, 28, 46-64, 86-89, 118-135, 149-150, 157-170, 203-219, 245-248 and 280-294, and does not contain a cysteine residue outside these positions, and which furthermore contains substitution of one or more amino acids Lys, Arg, Gln, Asn, Glu, Asp or His at positions 16-29, 59-74, 88-102, 135-145, 156-169, 202-231, 259-266 and 305-317 by Gly, Ala, Val, Ile, Leu, Ser, Thr, Met, Pro, Phe, or Tyr, preferably Gly, Ala, Val or Ser; herein the corresponding amino acid positions in other annexins apply, e.g. as depicted in FIG. 2. The annexins may be the proteins as such, or the conjugates with spacers and/or recognizable compounds. The cysteine residue(s) may be substituted, e.g. with a recognizable group (A).

The complexes of the annexin variant and the recognizable compound A can be used in a therapeutic or diagnostic method for targeting a medicament or a diagnostic agent to a specific site, in particular to cells which expose PS. In such a method, a composition containing the complex of the annexin variant and the recognizable compound A is first administered to a subject for which such therapeutic or diagnostic method is intended, followed by administering to the subject a composition comprising at least one complex comprising a compound B recognizing and binding to compound A and a diagnostic or therapeutic compound. Compound B is especially a specific counterpart of compound A, for example streptavidin or avidin, in case compound A is biotin. Likewise, compound B may be biotin or a complex of multiple biotins, especially if compound A is streptavidin or avidin. Compound B may also be an oligonucleotide, a morpholino, a PNA or an aptamer which have high affinity for the oligonucleotide, morpholino, PNA or aptamer counterpart bound to the annexin molecule as described above. It may also be a receptor or a part thereof, where compound A is the receptor ligand, or vice versa. Also compound may be an antigen to an antibody as compound A or fragment thereof or vice versa.

The diagnostic agent that can be used in the diagnostic method of the invention, can be selected from a fluorescent group, a radionuclide, an MRI contrast agent, a CT contrast agent, an ultrasound agent, and a combination thereof. Suitable examples of fluorescent groups are fluoresceines, Alexas, Phycoerythrines, Cy-compounds, Nanocrystals and a combination thereof. Suitable examples of radionuclides include Carbon-11, Fluorine-18, Indium-111, Iodine-123, Iodine-131, Nitrogen-13, Oxygen-15, Technetium-99m, Zirconium-89, Ga-67, Ga-68, Cu-64 and a combination thereof, which are incorporated in suitable molecules bound to compound B or in compound B itself. An MRI contrast agent may be selected from Gadolinium, magnetic particles and paramagnetic particles.

Therapeutic compounds that can be used in the therapeutic method of the invention, can for example be a toxin, an enzyme, enzyme inhibitors, a lipid, a carbohydrate, an immunoglobulin or a fragment thereof, an immunoconjugate, a chemotherapeutic compound, a photosensitizer, a radionuclide, a cell death inducing agent, a cell death inhibiting agent, a fibrinolytic compound, and a combination thereof. The toxin can be selected from Dt, PE, P38, P40, ricin, abrin, diphtheria toxin, cholera toxin, gelonin, pseudomonas, exotoxin, shigella toxin, pokeweed antiviral protein, and a combination thereof. Examples of enzymes that can be coupled to compound B include peroxidases, alkalases, caspases, and a combination thereof. Lipids can e.g. be selected from phospholipids, fatty acids, terpenes, steroids, and a combination thereof. The lipid can be embedded in the membrane of a liposome.

Examples of chemotherapeutic agents include BiCNU, bleomycin, busulfan, CCNU, carboplatin, carmustine, cisplatin, cisplatinum, chlorambucil, 2-cholrodeoxyadenosine, cladirabine, cytarabine, cyclophosphamide, dacarbazine, daunorubicin, docetaxel, doxorubicin, DTIC, etoposide, 5-flourouracil, fludarabine, gemcitabine, hydroxyurea, idarubicin, ifosfamide, irinotecan, lomustine, melphelan, methotrexate, mithramycin, mitomycin, mitoxantrone, nitrogen mustard, oxaliplatin, paclitaxel, plicamycin, procarbazine, raltritexed, semustine, tomudex, topotecan, vinblastine, vincristine, vinorelbine, and combinations thereof.

Examples of photo sensitizers include phthalocyanines, rhodoporphyrins, rhodochlorins, mesorhodochlorins, phylloerythrin and its derivatives, porphorin and its derivatives, metal-pyrollic compounds, and combinations thereof.

Cell death inducing agents that can advantageously be used in the method of the invention can be selected from the group of apoptosis inducers, kinase inhibitors, activators of mitochondrial permeability transition activators, polynucleotides encoding for a cell death inducing protein, activators of ion-transport across the membrane, polynucleotides being an anti-sense to polynucleotides encoding for cell death inhibiting proteins, polynucleotides interacting with and inhibiting cell death inhibiting proteins, and a combination thereof.

Examples of therapeutic radionuclides include $^{32}P$, $^{89}Sr$, $^{90}Y$, $^{103}Pd$, $^{125}I$, $^{131}I$, $^{137}Cs$, $^{153}Sm$, $^{186}Re$, $^{188}Re$, $^{192}Ir$, $^{64}Cu$, $^{67}Cu$, $^{67}Ga$, $^{86}Y$, $^{105}Rh$, $^{111}In$, $^{114m}In$, $^{124}I$, $^{149}Pm$, $^{166}Ho$, $^{169}Yb$, $^{177}Lu$, $^{211}At$, $^{213}Bi$, $^{225}A$.

The therapeutic and diagnostic compounds can be bound to compound B by methods known in the art. For example, when the therapeutic or diagnostic compound is a protein, it can be coupled through a lysine or arginine residue, optionally after activation using cyanogen bromide or other chemical or physical methods. If the compound is a lipid, such as phosphatidylethanolamine, it can be coupled to the amino group using methods known in the art. If the compound is a polynucleotide it can be coupled for example to hydroxyl groups thereof using methods known in the art. If the compound is a radionuclide, it can be coupled either directly or indirectly by coupling a chelator to compound B that chelates the radionuclide of choice.

The complex can also be used for detecting the presence or absence of cells or cell particles expressing phospholipids comprising:

a) administering to a subject a composition comprising at least one complex comprising a recognizable compound A and an annexin or an annexin variant, and:

b) administering to a subject a composition comprising at least one complex comprising a compound B recognizing compound A and a diagnostic agent, and:

c) submitting a subject to a detecting step such as optical imaging, SPECT imaging, PET imaging, MRI imaging, CT imaging, and ultrasound imaging.

The invention also pertains to a diagnostic kit suitable for carrying out the diagnostic method as described above, which comprises at least a complex of an annexin variant and an affinity compound A, and optionally a complex of a detectable (reporter) compound and an affinity compound B, and optionally diluents and further components necessary for carrying a diagnostic method. Preferably, the complex of the annexin variant and the complex of the detectable compound are conditioned separately.

The invention also pertains to a pharmaceutical kit suitable for carrying out the therapeutic method as described above, which comprises at least a complex of an annexin variant and an affinity compound A combined with a pharmaceutically acceptable excipient, and optionally a complex of a therapeutic compound and an affinity compound B, and optionally diluents and further components necessary for carrying a therapeutic method. Preferably, the complex of the annexin variant and the complex of the therapeutic compound are conditioned separately.

The present invention provides methods and compositions for the treatment, diagnosis, prevention, and research of diseases, such as neoplastic diseases, neurodegenerative diseases, cardiovascular diseases, autoimmune diseases, and inflammatory diseases. The methods include the administration to subjects of targeting complexes comprising annexins and annexin variants and diagnostic and therapeutic complexes comprising molecular imaging agents and pharmaceutical compounds respectively.

The present invention relates to the ability of annexins to bind to PS expressing cells. The present invention relates to the use of annexins in pretargeting methods to diagnose and treat diseases. It is known that annexins are taken up by liver, spleen and kidneys and by the reticulo-endothelial system of the bone marrow. Injecting annexins conjugated to diagnostic compounds and therapeutic compounds will result in high background signals and undesired toxic side-effects respectively. Therefore, the present invention provides methods in which annexins will be conjugated neither to diagnostic compounds such as fluorescent groups, radionuclides, MRI contrast agents, CT contrast agents and ultrasound agents nor to therapeutic compounds such as a toxin, an enzyme, a lipid, a carbohydrate, an immunoglobulin or a fragment thereof, an immunoconjugate, a chemotherapeutic compound, a photosensitizer, a radionuclide, a cell death inducing agent, a cell death inhibiting agent, a fibrinolytic compound prior to their administration into the subject. Instead, the present invention provides methods in which annexins be coupled to recognizable compounds A, which are selected from the set comprising but not restricted to biotin, multiple biotins, streptavidin, avidin, DNA, RNA, morpholinos, PNAs, aptamers, receptors and receptor ligands and antibodies. The present invention provides methods for delivering a diagnostic or a therapeutic compound to a target cell by delivering a complex of an annexin and a recognizable compound A to the target cell and by delivering subsequently a complex of a compound B that recognizes compound A and a diagnostic compound or a therapeutic compound to the target cell. The conjugated annexins will be administered to the subject. After a period of time, for example between 1 h and 24 h, the diagnostic or the therapeutic complex with compound B, which has a high affinity for compound A, will be injected into the same subject. Compound B will accumulate at sites where annexins conjugated to compound A are bound to cellular surfaces.

Annexins constitute a multigene family of proteins that share structural and functional features. The annexin polypeptide is organized in domains that form the so-called Annexin fold in space (Gerke and Moss, *Physiol. Rev.* 82:331-71 (2002)). The domains contain calcium binding sites through which an interaction with phospholipid membranes can occur. Once bound to a phospholipid surface the annexins can form a two-dimensional lattice through protein-protein interactions (Oling et al., *J. Mol. Biol.* 304: 561-73 (2001)). The physiological significances of the annexins are poorly understood but are thought to be related to their phospholipid binding activity. The annexins do not have a signal sequence and are therefore thought to play a role within the cell. Extracellular localization of annexins has been reported but it is unknown whether this has happened by a selective process or by an aspecific event such as cell lysis. According to WO 2006/003488, annexins and annexin-Cys variants will induce their own internalization after binding to cell surface expressed PS. The phenomenon of internalization reduces the efficacy of the pretargeting strategy. The present invention relates to annexins that are not internalized by the target cells. In order to find annexin variants that are less internalized the mechanism of internalization was inspected on its structure-function relationships. The internalization is induced by the formation of annexin trimers that form a 2-dimensional network on the phospholipid bilayer (Kenis et al., *J. Biol. Chem.* 279:52623-9 (2004)). The annexin trimers arise from non-covalent interactions between annexin molecules.

BRIEF DESCRIPTION OF THE DRAWINGS

FIG. 1 depicts the amino acid sequence for annexin A5.
FIG. 2 depicts an amino acid sequence alignment between human annexins A1, A2, A3, A4, A5, A6, A7, A8, A9, A10, A11, and A13.

EXAMPLE 1

Production of Annexin A5-2D Variants Having One or More Amino Acids at Positions 62, 69, 100, 137, 138 and 159 Replaced by Alanine and Glycine The human annexin A5 cDNA was prepared from a white blood cell cDNA library from a healthy volunteer with standard techniques known in the art. The cDNA sequence encoded the amino acid sequence presented in FIG. 1. Primers were designed to mutate annexin A5 by PCR techniques such that the resulting cDNA encoded the amino acid sequence of FIG. 1 with the exception of the following substitutions, that were performed singularly, but also in combinations thereof in the cDNA: R62A, K69A, K100A, E137A, D138G, and N159A. The annotation employs the single letter code for amino acids and the numerical position in the amino acid sequence where the substitution occurs with left to the number presenting the original amino acid and right to the number presenting the substitute.

The annexin A5-2D cDNA was cloned into a bacterial expression vector with standard techniques known in the art. *E. Coli* transformed with the resulting bacterial expression vectors were grown in a fermentor. The annexin A5-2D variants that were produced by the bacteria were isolated and purified from *E. Coli* lysates with standard chromatography techniques known to persons skilled in the art.

The purified annexin A5-2D variant appeared as a homogenous band of around 34 kDa on SDS-PAGE and exhibited full calcium-dependent phosphatidylserine binding activity as measured by plasmon surface resonance technique using the BiaCore.

EXAMPLE 2

Production of Annexin A5-2D Variants Having One or More Amino Acids at Positions 62, 69, 100, 137, 138 and 159 Replaced by Alanine and Glycine and Having Glutamine at Position 2 Replaced by Cysteine The annexin A5-2D cDNA was prepared as described in Example 1 of the present invention. Primers were designed to mutate annexin A5-2D cDNA by PCR techniques such that the resulting cDNA encoded the amino acid sequence of an annexin A5-2D variant with the exception that the amino acid Glutamine at position 2 was replaced by the amino acid Cysteine.

The purified annexin A5-2D-Cys2 variant appeared as a homogenous band of around 34 kDa on SDS-PAGE and exhibited full calcium-dependent phosphatidylserine binding activity as measured by plasmon surface resonance technique using the BiaCore.

EXAMPLE 3

Production of Annexin A5-2D Variants Having One or More Amino Acids at Positions 62, 69, 100, 137, 138 and 159 Replaced by Alanine and Glycine and Having Glycine at Position 165 Replaced by Cysteine The annexin A5-2D cDNA was prepared as described in Example 1 of the present invention. Primers were designed to mutate annexin A5-2D cDNA by PCR techniques such that the resulting cDNA encoded the amino acid sequence of an annexin A5-2D variant with the exception that the amino acid Glycine at position 165 was replaced by the amino acid Cysteine.

The purified annexin A5-2D-Cys165 variant appeared as a homogenous band of around 34 kDa on SDS-PAGE and exhibited full calcium-dependent phosphatidylserine binding activity as measured by plasmon surface resonance technique using the BiaCore.

EXAMPLE 4

Binding of Annexin A5-2D Variants Having One or More Amino Acids at Positions 62, 69, 100, 137, 138 and 159 Replaced by Alanine and Glycine to Phospholipid Bilayers This example demonstrates that the annexin A5-2D variant has a calcium-dependent ability to bind to PS of phospholipid bilayers like annexin A5 but lacks the ability to form a 2-dimensional network on the phospholipid surface and is not internalized into a cell.

The binding of annexin A5-2D to a phospholipid bilayer containing PS was studied by ellipsometry (Andree et al., *J. Biol. Chem.* 265:4923-4928 (1990)). In the absence of calcium the annexin A5-2D variant did not bind to the phospholipid surface by increasing the calcium concentration an increase in binding was observed similar to the calcium-dependent binding isotherm of annexin A5.

Annexin A5-2D bound to a phospholipid surface was analysed by electron microscopy (Mosser et al., *J. Mol. Biol.*

271:241-5 (1991)). Unlike annexin A5, the annexin A5-2D variant did not form an ordered 2-dimensional network.

Jurkat cells were co-incubated with fluorescent annexin A5-2D or fluorescent annexin A5, and the apoptotic stimulus. The cells were analysed for the localization of fluorescent annexin A5-2D or fluorescent annexin A5 by confocal scanning laser microscopy (Kenis et al., *J. Biol. Chem.* 279:52623-9 (2004)). Annexin A5 was internalized. Annexin A5-2D was not internalized but remained bound to the plasma membrane.

EXAMPLE 5

The Coupling of Maleimide-Activated Biotin to the Annexin A5-2D Variant Having Amino Acids at Positions 62, 69, 100, 137, 138 and 159 Replaced by Alanine and Glycine and Having Glutamine at position 2 and Cysteine at Position 315 Replaced by Cysteine and Serine Respectively The annexin A5-2D variant was prepared as described by example 2. The Cysteine was removed at position 315 and incorporated at position 2 in order to be able to couple compounds easily to the annexin A5-2D variant through thiol-chemistry without affecting the PS binding activity of the annexin A5-2D variant.

EZ-Link PEO-Maleimide activated biotin (Pierce) was dissolved in 25 mM Hepes/-NaOH, pH 7.0, 140 mM NaCl, 1 mM EDTA at a concentration of 10 mM. 3.4 mg/ml annexin A5-2D variant was dialysed into 25 mM Hepes/NaOH, pH 7.0, 140 mM NaCl, 1 mM EDTA. 200 μl biotin solution was added to 1 ml annexin A5-2D variant. The mixture was incubated for 120 minutes at 37° C. and thereafter dialysed into 25 mM Hepes/NaOH, pH 7.4, 140 mM NaCl, 1 mM EDTA.

The resulting conjugate was assayed on its PS binding activity by ellipsometry and tested for the accessibility of the biotin group using avidin (Pierce). The biotinylated annexin A5-2D showed no impaired PS binding, while the avidin readily bound to the biotinylated annexin A5-2D on the phospholipid surface.

EXAMPLE 6

The Coupling of Maleimide-Activated Avidin to the Annexin A5-2D Variant Having Amino Acids at Positions 62, 69, 100, 137, 138 and 159 Replaced by Alanine and Glycine and Having Glutamine at position 2 and Cysteine at Position 315 replaced by Cysteine and Serine Respectively The annexin A5-2D variant was prepared as described by example 2. The Cysteine was removed at position 315 and incorporated at position 2 in order to be able to couple compounds easily to the annexin A5-2D variant through thiol chemistry without affecting the PS binding activity of the annexin A5-2D variant.

Immunopure avidin (Pierce) was dissolved in 25 mM Hepes/NaOH, pH 7.4, 140 mM NaCl at a concentration of 8 mg/ml. 1 mg of Sulfo-SMCC (Pierce) was added to the avidin solution and the mixture was incubated for 60 minutes at room temperature. The excess cross-linker was removed by gel-filtration on a PD 10 column (GE-Amersham/-Pharmacia). The maleimide activated avidin was added to 1 mg/ml of annexin A5-2D variant that was dialysed into 25 mM Hepes/NaOH, pH 7.0, 140 mM NaCl, 1 mM EDTA. The mixture was incubated for 120 minutes at 37° C.

The conjugate between avidin and the annexin A5-2D variant was tested on its ability to bind to PS by ellipsometry. The conjugate showed no impaired PS binding properties.

EXAMPLE 7

A procedure to Visualize a Tumor In Vivo Using Annexin A5-2D Variant and Pretargeting Annexin A5-2D variants having a Cysteine at position 2 or 165 were engineered and produced as presented in examples 2 and 3, respectively. The Cys-annexin A5-2D variants were biotinylated using maleimide-biotin as described by example 5.

Biotinylated annexin A5-2D was injected intravenously into a tumor-bearing mouse. Levels of circulating biotinylated annexin A5-2D were decreased either by time-lapsed spontaneous clearance or by forced clearance with for example intravenously administered avidin. Streptavidin conjugated to a molecular imaging probe such as for example a fluorescent compound or a radionuclide was injected intravenously. The mouse was then subjected to imaging using a whole body optical imager if streptavidin conjugated to a fluorescent probe was used or using a SPECT, PET, SPECT/CT or PET/CT imager if streptavidin conjugated to a radio-nuclide was used.

This visualization procedure can be applied for localizing and quantifying tumors and metastases and for determination of the efficacy of an anti-tumor therapy.

EXAMPLE 8

A Procedure to Visualize Unstable Atherosclerotic Plaques In Vivo Using Annexin A5-2D Variant and Pretargeting Annexin A5-2D variants having a Cysteine at position 2 or 165 were engineered and produced as presented in examples 2 and 3, respectively. The Cys-annexin A5-2D variants were biotinylated using maleimide-biotin as described by example 5.

Biotinylated annexin A5-2D was injected intravenously into a mouse suffering from atherosclerotic lesions. Levels of circulating biotinylated annexin A5-2D were decreased either by time-lapsed spontaneous clearance or by forced clearance with for example intravenously administered avidin. Streptavidin conjugated to a molecular imaging probe such as for example a fluorescent compound or a radionuclide was injected intravenously. The mouse was then subjected to imaging using a whole body optical imager if streptavidin conjugated to a fluorescent probe was used or using a SPECT, PET, SPECT/CT or PET/CT imager if streptavidin conjugated to a radio-nuclide was used.

This visualization procedure can be applied for localizing unstable atherosclerotic plaques and distinguishing unstable atherosclerotic plaques from stable atherosclerotic plaques. The visualization procedure can be applied to determine the efficacy of drugs that stabilize unstable atherosclerotic plaques.

EXAMPLE 9

A Procedure to Treat a Tumor In Vivo Using Annexin A5-2D Variant and Pretargeting Annexin A5-2D variants having a Cysteine at position 2 or 165 were engineered and produced as presented in examples 2 and 3, respectively. The Cys-annexin A5-2D variants were biotinylated using maleimide-biotin as described by example 5. Biotinylated annexin A5-2D was injected intravenously into a tumor-bearing mouse. Levels of circulating biotinylated annexin A5-2D were decreased either by time-lapsed spontaneous clearance or by forced clearance with for example intravenously administered avidin. Streptavidin conjugated to an antic-cancer compound such as for example doxorubicin and cisplatin, or conjugated to a carrier of anti-cancer compounds such as for example liposomes encapsulating for example doxorubicin and cisplatin was injected intravenously.

This pretargeting therapeutic procedure can be applied to delivering locally anti-cancer drugs to the tumor.

EXAMPLE 10

A Procedure to Treat Unstable Atherosclerotic Plaques In Vivo Using Annexin A5-2D Variant and Pretargeting Annexin A5-2D variants having a Cysteine at position 2 or 165 were engineered and produced as presented in examples 2 and 3, respectively. The Cys-annexin A5-2D variants were biotinylated using maleimide-biotin as described by example 5.

Biotinylated annexin A5-2D was injected intravenously into a mouse suffering from atherosclerotic lesions. Levels of circulating biotinylated annexin A5-2D were decreased either by time-lapsed spontaneous clearance or by forced clearance with for example intravenously administered avidin. Streptavidin conjugated to atherosclerotic plaque stabilizing compound such as for example statins and anti-inflammatory compounds, or conjugated to a carrier of atherosclerotic plaque stabilizing compounds such as for example liposomes encapsulating for example statins and anti-inflammatory compounds was injected intravenously.

This pretargeting therapeutic procedure can be applied to delivering locally atherosclerotic plaque stabilizing compounds to the atherosclerotic plaques.

All of the examples, methods and/or compositions disclosed, and claimed herein can be made and executed without undue experimentation in light of the present disclosure. While the methods and compositions of this invention have been described in terms of preferred embodiments, it will be apparent to those skilled in the art that variations may be applied to the methods and/or compositions and in the steps or in the sequence of steps of the methods described herein without departing from the concept, spirit and scope of the invention. It will be apparent to those skilled in the art that compositions with compounds which are structurally and functionally related may be substituted for compositions with the compounds described herein.

The invention claimed is:

1. An annexin conjugate comprising a variant of annexin A5 covalently bound to a recognizable compound; wherein the annexin A5 comprises the amino acid sequence of SEQ ID NO:1 and one or more polar amino acids selected from Glu, Gln, Asp, Asn, Arg and Lys, in helices IA, ID, IIA, IID, IIIC, IIID and IVE and in stretches connecting helices IC and ID, IIE and IIIA, IIIC and IIID, IIID and IIIE, and IVA and IVB, of SEQ ID NO: 1 is replaced by a non-polar amino acid to impair internalisation of the variant of annexin A5 into a cell, wherein the recognizable compound is bound to a cysteine residue of the variant of annexin A5, and wherein the variant of annexin A5 binds to at least one phospholipid.

2. The annexin conjugate according to claim 1, wherein the one or more amino acids are located at positions 16-29, 59-74, 88-102, 135-145, 156-169, 202-231, 259-266 and 305-317 of SEQ ID NO:1.

3. The annexin conjugate according to claim 1, wherein at least two of the one or more amino acids are replaced by non-polar amino acids.

4. The annexin conjugate according to claim 1, wherein the recognizable compound is selected from one or more biotins, avidin or streptavidin, oligonucleotides or morpholinos, peptide nucleic acids and aptamers, receptors or parts thereof, receptor ligands or parts thereof, antibodies or fragments thereof, and antigens.

5. The annexin conjugate according to claim 1, wherein the variant of annexin A5 comprise a cysteine residue at one of the amino acid positions 1-15, 46-58, 86-87, 118-134, 162-167, 245-248 and 280-294 of SEQ ID NO: 1, and the variant of annexin A5 does not have a cysteine residue at the positions 20-23, 25-27, 29-45, 65-85, 90-117, 136-148, 151-156, 171-202, 220-244, 249-279 and 295-319 of SEQ ID NO:1.

6. The annexin conjugate according to claim 1, wherein the recognizable, compound is selected from one or more biotins, avidin or streptavidin, oligonucleotides or morpholinos, peptide nucleic acids and aptamers, receptors, receptor ligands, and antibodies.

7. An isolated variant of annexin A5, wherein the annexin A5 comprises SEQ ID NO:1, wherein the variant of annexin A5 consists of the following modifications to SEQ ID NO:1:
(1) one or more amino acids selected from polar amino acids Glu, Gln, Asp, Asn, Arg, Lys and His at positions 16-29, 59-74, 88-102, 135-145, 156-169, 202-231, 259-266 and 305-317 of SEQ ID NO:1, are replaced by Gly, Ala, Val, Ile, Leu, Ser, Thr, Met, Pro, Phe, or Tyr, and
(2) one or more amino acids at positions 1-19, 24, 28, 46-64, 86-89, 118-135, 149-150, 157-170, 203-219, 245-248 and 280-294 of SEQ ID NO:1 are replaced by a cysteine residue, and
wherein the variant of annexin A5 has impaired ability to induce internalisation into a cell.

8. The isolated variant of annexin A5 according to claim 7, wherein the cysteine residue is bound to a recognizable compound.

9. A kit comprising:
   a) at least one annexin conjugate according to claim 1; and,
   b) a diagnostic or therapeutic compound capable of recognizing the recognizable compound bound to the variant of annexin A5.

10. A method for delivering a diagnostic compound to a target cell in a subject comprising:
   a) administering to the subject a composition comprising at least one annexin conjugate according to claim 1, and
   b) administering to the subject a composition comprising at least one complex of a recognizing compound which recognizes and binds to the recognizable compound bound to the variant of annexin A5 and a diagnostic compound.

11. The method according to claim 10, wherein the diagnostic agent is selected from the group consisting of a fluorescent group, a radionuclide, an MRI contrast agent, a CT contrast agent, an ultrasound agent, and a combination thereof.

12. The method according to claim 10, wherein the recognizing compound is selected from streptavidin or avidin, biotin or a complex of multiple biotins, an oligonucleotide or a morpholino, peptide nucleic acids and aptamers, a receptor or a part thereof, a receptor ligand or a part thereof, an antibody or a fragment thereof, and an antigen.

13. A method for delivering a pharmaceutical compound to a target cell in a subject comprising:
   a) administering to the subject a composition comprising at least one annexin conjugate according to claim 1, and
   b) administering to the subject a composition comprising at least one complex of a recognizing compound which recognizes and binds to the recognizable compound bound to the variant of annexin A5 and a pharmaceutical compound.

14. The method according to claim 13, wherein the pharmaceutical compound is selected from the group consisting of a toxin, an enzyme, an enzyme inhibitor, a lipid, a carbohydrate, an immunoglobulin or a fragment thereof, an immunoconjugate, a chemo-therapeutic compound, a photosensitizer, a radionuclide, a cell death inducing agent, a cell death inhibiting agent, a fibrinolytic compound, and a combination thereof.

15. The method according to claim 13, wherein the recognizing compound is selected from streptavidin or avidin, biotin or a complex of multiple biotins, an oligonucleotide or a morpholino, peptide nucleic acids and aptamers, a receptor or a part thereof, a receptor ligand or a part thereof, an antibody or a fragment thereof, and an antigen.

* * * * *

SEQUENCE LISTING

```
<160> NUMBER OF SEQ ID NOS: 13

<210> SEQ ID NO 1
<211> LENGTH: 319
<212> TYPE: PRT
<213> ORGANISM: Homo sapiens

<400> SEQUENCE: 1

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
                20                  25                  30

Asp Glu Glu Ser Ile Leu Thr Leu Leu Thr Ser Arg Ser Asn Ala Gln
            35                  40                  45

Arg Gln Glu Ile Ser Ala Ala Phe Lys Thr Leu Phe Gly Arg Asp Leu
        50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
```

```
            180                 185                 190
Phe Ile Thr Ile Phe Gly Thr Arg Ser Val Ser His Leu Arg Lys Val
        195                 200                 205
Phe Asp Lys Tyr Met Thr Ile Ser Gly Phe Gln Ile Glu Glu Thr Ile
        210                 215                 220
Asp Arg Glu Thr Ser Gly Asn Leu Glu Gln Leu Leu Leu Ala Val Val
225                 230                 235                 240
Lys Ser Ile Arg Ser Ile Pro Ala Tyr Leu Ala Glu Thr Leu Tyr Tyr
                245                 250                 255
Ala Met Lys Gly Ala Gly Thr Asp Asp His Thr Leu Ile Arg Val Met
            260                 265                 270
Val Ser Arg Ser Glu Ile Asp Leu Phe Asn Ile Arg Lys Glu Phe Arg
        275                 280                 285
Lys Asn Phe Ala Thr Ser Leu Tyr Ser Met Ile Lys Gly Asp Thr Ser
        290                 295                 300
Gly Asp Tyr Lys Lys Ala Leu Leu Leu Leu Cys Gly Glu Asp Asp
305                 310                 315

<210> SEQ ID NO 2
<211> LENGTH: 318
<212> TYPE: PRT
<213> ORGANISM: Homo sapiens

<400> SEQUENCE: 2

Lys Gly Gly Pro Gly Ser Ala Val Ser Pro Tyr Pro Thr Phe Asn Pro
1               5                   10                  15
Ser Ser Asp Val Ala Ala Leu His Lys Ala Ile Met Val Lys Gly Val
            20                  25                  30
Asp Glu Ala Thr Ile Ile Asp Ile Leu Thr Lys Arg Asn Asn Ala Gln
        35                  40                  45
Arg Gln Gln Ile Lys Ala Ala Tyr Leu Gln Glu Thr Gly Lys Pro Leu
    50                  55                  60
Asp Glu Thr Leu Lys Lys Ala Leu Thr Gly His Leu Glu Glu Val Val
65                  70                  75                  80
Leu Ala Leu Leu Lys Thr Pro Ala Gln Phe Asp Ala Asp Glu Leu Arg
                85                  90                  95
Ala Ala Met Lys Gly Leu Gly Thr Asp Glu Asp Thr Leu Ile Glu Ile
            100                 105                 110
Leu Ala Ser Arg Thr Asn Lys Glu Ile Arg Asp Ile Asn Arg Val Tyr
        115                 120                 125
Arg Glu Glu Leu Lys Arg Asp Leu Ala Lys Asp Ile Thr Ser Asp Thr
    130                 135                 140
Ser Gly Asp Phe Arg Asn Ala Leu Leu Ser Leu Ala Lys Gly Asp Arg
145                 150                 155                 160
Ser Glu Asp Phe Gly Val Asn Glu Asp Leu Ala Asp Ser Asp Ala Arg
                165                 170                 175
Ala Leu Tyr Glu Ala Gly Glu Arg Arg Lys Gly Thr Asp Val Asn Val
            180                 185                 190
Phe Asn Thr Ile Leu Thr Thr Arg Ser Tyr Pro Gln Leu Arg Arg Val
        195                 200                 205
Phe Gln Lys Tyr Thr Lys Tyr Ser Lys His Asp Met Asn Lys Val Leu
    210                 215                 220
Asp Leu Glu Leu Lys Gly Asp Ile Glu Lys Cys Leu Thr Ala Ile Val
225                 230                 235                 240
Lys Cys Ala Thr Ser Lys Pro Ala Phe Phe Ala Glu Lys Leu His Gln
```

```
                      245                 250                 255
Ala Met Lys Gly Val Gly Thr Arg His Lys Ala Leu Ile Arg Ile Met
                260                 265                 270

Val Ser Arg Ser Glu Ile Asp Met Asn Asp Ile Lys Ala Phe Tyr Gln
            275                 280                 285

Lys Met Tyr Gly Ile Ser Leu Cys Gln Ala Ile Leu Asp Glu Thr Lys
        290                 295                 300

Gly Asp Tyr Glu Lys Ile Leu Val Ala Leu Cys Gly Gly Asn
305                 310                 315

<210> SEQ ID NO 3
<211> LENGTH: 320
<212> TYPE: PRT
<213> ORGANISM: Homo sapiens

<400> SEQUENCE: 3

Pro Pro Ser Ala Tyr Gly Ser Val Lys Ala Tyr Thr Asn Phe Asp Ala
1               5                   10                  15

Glu Arg Asp Ala Leu Asn Ile Glu Thr Ala Ile Lys Thr Lys Gly Val
            20                  25                  30

Asp Glu Val Thr Ile Val Asn Ile Leu Thr Asn Arg Ser Asn Ala Gln
        35                  40                  45

Arg Gln Asp Ile Ala Phe Ala Tyr Gln Arg Arg Thr Lys Lys Glu Leu
    50                  55                  60

Ala Ser Ala Leu Lys Ser Ala Leu Ser Gly His Leu Glu Thr Val Ile
65                  70                  75                  80

Leu Gly Leu Leu Lys Thr Pro Ala Gln Tyr Asp Ala Ser Glu Leu Lys
                85                  90                  95

Ala Ser Met Lys Gly Leu Gly Thr Asp Glu Asp Ser Leu Ile Glu Ile
            100                 105                 110

Ile Cys Ser Arg Thr Asn Gln Glu Leu Gln Glu Ile Asn Arg Val Tyr
        115                 120                 125

Lys Glu Met Tyr Lys Thr Asp Leu Glu Lys Asp Ile Ile Ser Asp Thr
    130                 135                 140

Ser Gly Asp Phe Arg Lys Leu Met Val Ala Leu Ala Lys Gly Arg Arg
145                 150                 155                 160

Ala Glu Asp Gly Ser Val Ile Asp Tyr Glu Leu Ile Asp Gln Asp Ala
                165                 170                 175

Arg Asp Leu Tyr Asp Ala Gly Val Lys Arg Lys Gly Thr Asp Val Pro
            180                 185                 190

Lys Trp Ile Ser Ile Met Thr Glu Arg Ser Val Pro His Leu Gln Lys
        195                 200                 205

Val Phe Asp Arg Tyr Lys Ser Tyr Ser Pro Tyr Asp Met Leu Glu Ser
    210                 215                 220

Ile Arg Lys Glu Val Lys Gly Asp Leu Glu Asn Ala Phe Leu Asn Leu
225                 230                 235                 240

Val Gln Cys Ile Gln Asn Lys Pro Leu Tyr Phe Ala Asp Arg Leu Tyr
                245                 250                 255

Asp Ser Met Lys Gly Lys Gly Thr Arg Asp Lys Val Leu Ile Arg Ile
            260                 265                 270

Met Val Ser Arg Ser Glu Val Asp Met Leu Lys Ile Arg Ser Glu Phe
        275                 280                 285

Lys Arg Lys Tyr Gly Lys Ser Leu Tyr Tyr Ile Gln Gln Asp Thr
    290                 295                 300

Lys Gly Asp Tyr Gln Lys Ala Leu Leu Tyr Leu Cys Gly Gly Asp Asp
```

```
                305                 310                 315                 320

<210> SEQ ID NO 4
<211> LENGTH: 319
<212> TYPE: PRT
<213> ORGANISM: Homo sapiens

<400> SEQUENCE: 4

Trp Val Gly His Arg Gly Thr Val Arg Asp Tyr Pro Asp Phe Ser Pro
1               5                   10                  15

Ser Val Asp Ala Glu Ala Ile Gln Lys Ala Ile Arg Gly Ile Gly Thr
            20                  25                  30

Asp Glu Lys Met Leu Ile Ser Ile Leu Thr Glu Arg Ser Asn Ala Gln
        35                  40                  45

Arg Gln Leu Ile Val Lys Glu Tyr Gln Ala Ala Tyr Gly Lys Glu Leu
    50                  55                  60

Lys Asp Asp Leu Lys Gly Asp Leu Ser Gly His Phe Glu His Leu Met
65                  70                  75                  80

Val Ala Leu Val Thr Pro Pro Ala Val Phe Asp Ala Lys Gln Leu Lys
                85                  90                  95

Lys Ser Met Lys Gly Ala Gly Thr Asn Glu Asp Ala Leu Ile Glu Ile
            100                 105                 110

Leu Thr Thr Arg Thr Ser Arg Gln Met Lys Asp Ile Ser Gln Ala Tyr
        115                 120                 125

Tyr Thr Val Tyr Lys Lys Ser Leu Gly Asp Asp Ile Ser Ser Glu Thr
    130                 135                 140

Ser Gly Asp Phe Arg Lys Ala Leu Leu Thr Leu Ala Asp Gly Arg Arg
145                 150                 155                 160

Asp Glu Ser Leu Lys Val Asp Glu His Leu Ala Lys Gln Asp Ala Gln
                165                 170                 175

Ile Leu Tyr Lys Ala Gly Glu Asn Arg Trp Gly Thr Asp Glu Asp Lys
            180                 185                 190

Phe Thr Glu Ile Leu Cys Leu Arg Ser Phe Pro Gln Leu Lys Leu Thr
        195                 200                 205

Phe Asp Glu Tyr Arg Asn Ile Ser Gln Lys Asp Ile Val Asp Ser Ile
    210                 215                 220

Lys Gly Glu Leu Ser Gly His Phe Glu Asp Leu Leu Leu Ala Ile Val
225                 230                 235                 240

Asn Cys Val Arg Asn Thr Pro Ala Phe Leu Ala Glu Arg Leu His Arg
                245                 250                 255

Ala Leu Lys Gly Ile Gly Thr Asp Glu Phe Thr Leu Asn Arg Ile Met
            260                 265                 270

Val Ser Arg Ser Glu Ile Asp Leu Leu Asp Ile Arg Thr Glu Phe Lys
        275                 280                 285

Lys His Tyr Gly Tyr Ser Leu Tyr Ser Ala Ile Lys Ser Asp Thr Ser
    290                 295                 300

Gly Asp Tyr Glu Ile Thr Leu Leu Lys Ile Cys Gly Gly Asp Asp
305                 310                 315

<210> SEQ ID NO 5
<211> LENGTH: 318
<212> TYPE: PRT
<213> ORGANISM: Homo sapiens

<400> SEQUENCE: 5

Ala Thr Lys Gly Gly Thr Val Lys Ala Ala Ser Gly Phe Asn Ala Met
1               5                   10                  15
```

```
Glu Asp Ala Gln Thr Leu Arg Lys Ala Met Lys Gly Leu Gly Thr Asp
            20                  25                  30

Glu Asp Ala Ile Ile Ser Val Leu Ala Tyr Arg Asn Thr Ala Gln Arg
        35                  40                  45

Gln Glu Ile Arg Thr Ala Tyr Lys Ser Thr Ile Gly Arg Asp Leu Ile
50                  55                  60

Asp Asp Leu Lys Ser Glu Leu Ser Gly Asn Phe Glu Gln Val Ile Val
65                  70                  75                  80

Gly Met Met Thr Pro Thr Val Leu Tyr Asp Val Gln Glu Leu Arg Arg
                85                  90                  95

Ala Met Lys Gly Ala Gly Thr Asp Glu Gly Cys Leu Ile Glu Ile Leu
            100                 105                 110

Ala Ser Arg Thr Pro Glu Glu Ile Arg Arg Ile Ser Gln Thr Tyr Gln
        115                 120                 125

Gln Gln Tyr Gly Arg Ser Leu Glu Asp Asp Ile Arg Ser Asp Thr Ser
130                 135                 140

Phe Met Phe Gln Arg Val Leu Val Ser Leu Ser Ala Gly Gly Arg Asp
145                 150                 155                 160

Glu Gly Asn Tyr Leu Asp Asp Ala Leu Val Arg Gln Asp Ala Gln Asp
                165                 170                 175

Leu Tyr Glu Ala Gly Glu Lys Lys Trp Gly Thr Asp Glu Val Lys Phe
            180                 185                 190

Leu Thr Val Leu Cys Ser Arg Asn Arg Asn His Leu Leu His Val Phe
        195                 200                 205

Asp Glu Tyr Lys Arg Ile Ser Gln Lys Asp Ile Glu Gln Ser Ile Lys
210                 215                 220

Ser Glu Thr Ser Gly Ser Phe Glu Asp Ala Leu Leu Ala Ile Val Lys
225                 230                 235                 240

Cys Met Arg Asn Lys Ser Ala Tyr Phe Ala Glu Lys Leu Tyr Lys Ser
                245                 250                 255

Met Lys Gly Leu Gly Thr Asp Asp Asn Thr Leu Ile Arg Val Met Val
            260                 265                 270

Ser Arg Ala Glu Ile Asp Met Leu Asp Ile Arg Ala His Phe Lys Arg
        275                 280                 285

Leu Tyr Gly Lys Ser Leu Tyr Ser Phe Ile Lys Gly Asp Thr Ser Gly
290                 295                 300

Asp Tyr Arg Lys Val Leu Leu Val Leu Cys Gly Gly Asp Asp
305                 310                 315

<210> SEQ ID NO 6
<211> LENGTH: 319
<212> TYPE: PRT
<213> ORGANISM: Homo sapiens

<400> SEQUENCE: 6

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45

Arg Gln Glu Ile Ser Ala Ala Phe Lys Thr Leu Phe Gly Arg Asp Leu
50                  55                  60

Leu Asp Asp Leu Lys Ser Glu Leu Thr Gly Lys Phe Glu Lys Leu Ile
65                  70                  75                  80
```

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Val Val Gly Asp Thr
130                 135                 140

Ser Gly Tyr Tyr Gln Arg Met Leu Val Val Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
290                 295                 300

Gly Asp Tyr Lys Lys Ala Leu Leu Leu Leu Cys Gly Glu Asp Asp
305                 310                 315

<210> SEQ ID NO 7
<211> LENGTH: 324
<212> TYPE: PRT
<213> ORGANISM: Homo sapiens

<400> SEQUENCE: 7

Arg Val Glu Leu Lys Gly Thr Val Arg Pro Ala Asn Asp Phe Asn Pro
1               5                   10                  15

Asp Ala Asp Ala Lys Ala Leu Arg Lys Ala Met Lys Gly Leu Gly Thr
            20                  25                  30

Asp Glu Asp Thr Ile Ile Asp Ile Ile Thr His Arg Ser Asn Val Gln
        35                  40                  45

Arg Gln Gln Ile Arg Gln Thr Phe Lys Ser His Phe Gly Arg Asp Leu
    50                  55                  60

Met Thr Asp Leu Lys Ser Glu Ile Ser Gly Asp Leu Ala Arg Leu Ile
65                  70                  75                  80

Leu Gly Leu Met Met Pro Pro Ala His Tyr Asp Ala Lys Gln Leu Lys
                85                  90                  95

Lys Ala Met Glu Gly Ala Gly Thr Asp Glu Lys Ala Leu Ile Glu Ile
            100                 105                 110

Leu Ala Thr Arg Thr Asn Ala Glu Ile Arg Ala Ile Asn Glu Ala Tyr
        115                 120                 125

Lys Glu Asp Tyr His Lys Ser Leu Glu Asp Ala Leu Ser Ser Asp Thr
    130                 135                 140

```
Ser Gly His Phe Arg Arg Ile Leu Ile Ser Leu Ala Thr Gly His Arg
145                 150                 155                 160

Glu Glu Gly Gly Glu Asn Leu Asp Gln Ala Arg Glu Asp Ala Gln Val
            165                 170                 175

Ala Ala Glu Ile Leu Glu Ile Ala Asp Thr Pro Ser Gly Asp Lys Thr
        180                 185                 190

Ser Leu Glu Thr Arg Phe Met Thr Ile Leu Cys Thr Arg Thr Tyr Pro
    195                 200                 205

His Leu Arg Arg Val Phe Gln Glu Phe Ile Lys Met Thr Asn Tyr Asp
210                 215                 220

Val Glu His Thr Ile Lys Lys Glu Met Ser Gly Asp Val Arg Asp Ala
225                 230                 235                 240

Phe Val Ala Ile Val Gln Ser Val Lys Asn Lys Pro Leu Phe Phe Ala
                245                 250                 255

Asp Lys Leu Tyr Lys Ser Met Lys Gly Ala Gly Thr Asp Glu Lys Thr
            260                 265                 270

Leu Thr Arg Ile Met Val Ser Arg Ser Glu Ile Asp Leu Leu Asn Ile
        275                 280                 285

Arg Arg Glu Phe Ile Glu Lys Tyr Asp Lys Ser Leu His Gln Ala Ile
    290                 295                 300

Glu Gly Asp Thr Ser Gly Asp Phe Leu Lys Ala Leu Leu Ala Leu Cys
305                 310                 315                 320

Gly Gly Glu Asp

<210> SEQ ID NO 8
<211> LENGTH: 317
<212> TYPE: PRT
<213> ORGANISM: Homo sapiens

<400> SEQUENCE: 8

Thr Gln Val Thr Gln Gly Thr Ile Arg Pro Ala Ala Asn Phe Asp Ala
1               5                   10                  15

Ile Arg Asp Ala Glu Ile Leu Arg Lys Ala Met Lys Gly Phe Gly Thr
            20                  25                  30

Asp Glu Gln Ala Ile Val Asp Val Ala Asn Arg Ser Asn Asp Gln
        35                  40                  45

Arg Gln Lys Ile Lys Ala Ala Phe Lys Thr Ser Tyr Gly Lys Asp Leu
    50                  55                  60

Ile Lys Asp Leu Lys Ser Glu Leu Ser Gly Asn Met Glu Glu Leu Ile
65                  70                  75                  80

Leu Ala Leu Phe Met Pro Pro Thr Tyr Tyr Asp Ala Trp Ser Leu Arg
                85                  90                  95

Lys Ala Met Gln Gly Ala Gly Thr Gln Glu Arg Val Leu Ile Glu Ile
            100                 105                 110

Leu Cys Thr Arg Thr Asn Gln Glu Ile Arg Glu Ile Val Arg Cys Tyr
        115                 120                 125

Gln Ser Glu Phe Gly Arg Asp Leu Glu Lys Asp Ile Arg Ser Asp Thr
    130                 135                 140

Ser Gly His Phe Glu Arg Leu Leu Val Ser Met Cys Gln Gly Asn Arg
145                 150                 155                 160

Asp Glu Asn Gln Ser Ile Asn His Gln Met Ala Gln Glu Asp Ala Gln
                165                 170                 175

Arg Leu Tyr Gln Ala Gly Glu Gly Arg Leu Gly Thr Asp Glu Ser Cys
            180                 185                 190
```

```
Phe Asn Met Ile Leu Ala Thr Arg Ser Phe Pro Gln Leu Arg Ala Thr
            195                 200                 205

Met Glu Ala Tyr Ser Arg Met Ala Asn Arg Asp Leu Leu Ser Ser Val
    210                 215                 220

Ser Arg Glu Phe Ser Gly Tyr Val Glu Ser Gly Leu Lys Thr Ile Leu
225                 230                 235                 240

Gln Cys Ala Leu Asn Arg Pro Ala Phe Phe Ala Glu Arg Leu Tyr Tyr
                245                 250                 255

Ala Met Lys Gly Ala Gly Thr Asp Asp Ser Thr Leu Val Arg Ile Val
                260                 265                 270

Val Thr Arg Ser Glu Ile Asp Leu Val Gln Ile Lys Gln Met Phe Ala
            275                 280                 285

Gln Met Tyr Gln Lys Thr Leu Gly Thr Met Ile Ala Gly Asp Thr Ser
    290                 295                 300

Gly Asp Tyr Arg Arg Leu Leu Leu Ala Ile Val Gly Gln
305                 310                 315

<210> SEQ ID NO 9
<211> LENGTH: 320
<212> TYPE: PRT
<213> ORGANISM: Homo sapiens

<400> SEQUENCE: 9

Ile Glu Gln Glu Gly Val Thr Val Lys Ser Ser His Phe Asn Pro
1               5                   10                  15

Asp Pro Asp Ala Glu Thr Leu Tyr Lys Ala Met Lys Gly Ile Gly Thr
                20                  25                  30

Asn Glu Gln Ala Ile Ile Asp Val Leu Thr Lys Arg Ser Asn Thr Gln
            35                  40                  45

Arg Gln Gln Ile Ala Lys Ser Phe Lys Ala Gln Phe Gly Lys Asp Leu
    50                  55                  60

Thr Glu Thr Leu Lys Ser Glu Leu Ser Gly Lys Phe Glu Arg Leu Ile
65                  70                  75                  80

Val Ala Leu Met Tyr Pro Pro Tyr Arg Tyr Glu Ala Lys Glu Leu His
                85                  90                  95

Asp Ala Met Lys Gly Leu Gly Thr Lys Glu Gly Val Ile Ile Glu Ile
                100                 105                 110

Leu Ala Ser Arg Thr Lys Asn Gln Leu Arg Glu Ile Met Lys Ala Tyr
            115                 120                 125

Glu Glu Asp Tyr Gly Ser Ser Leu Glu Glu Asp Ile Gln Ala Asp Thr
    130                 135                 140

Ser Gly Tyr Leu Glu Arg Ile Leu Val Cys Leu Leu Gln Gly Ser Arg
145                 150                 155                 160

Asp Asp Val Ser Ser Phe Val Asp Pro Ala Leu Ala Leu Gln Asp Ala
                165                 170                 175

Gln Asp Leu Tyr Ala Ala Gly Glu Lys Ile Arg Gly Thr Asp Glu Met
                180                 185                 190

Lys Phe Ile Thr Ile Leu Cys Thr Arg Ser Ala Thr His Leu Leu Arg
            195                 200                 205

Val Phe Glu Glu Tyr Glu Lys Ile Ala Asn Lys Ser Ile Glu Asp Ser
    210                 215                 220

Ile Lys Ser Glu Thr His Gly Ser Leu Glu Glu Ala Met Leu Thr Val
225                 230                 235                 240

Val Lys Cys Thr Gln Asn Leu His Ser Tyr Phe Ala Glu Arg Leu Tyr
                245                 250                 255
```

```
Tyr Ala Met Lys Gly Ala Gly Thr Arg Asp Gly Thr Leu Ile Arg Asn
            260                 265                 270

Ile Val Ser Arg Ser Glu Ile Asp Leu Asn Leu Ile Lys Cys His Phe
        275                 280                 285

Lys Lys Met Tyr Gly Lys Thr Leu Ser Ser Met Ile Met Glu Asp Thr
    290                 295                 300

Ser Gly Asp Tyr Lys Asn Ala Leu Leu Ser Leu Val Gly Ser Asp Pro
305                 310                 315                 320

<210> SEQ ID NO 10
<211> LENGTH: 317
<212> TYPE: PRT
<213> ORGANISM: Homo sapiens

<400> SEQUENCE: 10

Ala Trp Gly Thr Leu Gly Thr Leu Arg Thr Phe Leu Asn Phe Ser Val
1               5                   10                  15

Asp Lys Asp Ala Gln Arg Leu Leu Arg Ala Ile Thr Gly Gln Gly Val
            20                  25                  30

Asp Arg Ser Ala Ile Val Asp Val Leu Thr Asn Arg Ser Arg Glu Gln
        35                  40                  45

Arg Gln Leu Ile Ser Arg Asn Phe Gln Glu Arg Thr Gln Gln Asp Leu
    50                  55                  60

Met Lys Ser Leu Gln Ala Leu Ser Gly Asn Leu Glu Arg Ile Val
65                  70                  75                  80

Met Ala Leu Leu Gln Pro Thr Ala Gln Phe Asp Ala Gln Glu Leu Arg
                85                  90                  95

Thr Ala Leu Lys Ala Ser Asp Ser Ala Val Asp Val Ala Ile Glu Ile
            100                 105                 110

Leu Ala Thr Arg Thr Pro Pro Gln Leu Gln Glu Cys Leu Ala Val Tyr
        115                 120                 125

Lys His Asn Phe Gln Val Glu Ala Val Asp Gly Ile Thr Ser Glu Thr
    130                 135                 140

Ser Gly Ile Leu Gln Asp Leu Leu Ala Leu Ala Lys Gly Gly Arg
145                 150                 155                 160

Asp Ser Tyr Ser Gly Ile Ile Asp Tyr Asn Leu Ala Glu Gln Asp Val
                165                 170                 175

Gln Ala Leu Gln Arg Glu Gly Pro Ser Arg Glu Thr Trp Val Pro
            180                 185                 190

Val Phe Thr Gln Arg Asn Pro Glu His Leu Ile Arg Val Phe Asp Gln
        195                 200                 205

Tyr Gln Arg Ser Thr Gly Gln Glu Leu Glu Glu Ala Val Gln Asn Arg
    210                 215                 220

Phe His Gly Asp Ala Gln Val Ala Leu Leu Gly Leu Ala Ser Val Ile
225                 230                 235                 240

Lys Asn Thr Pro Leu Tyr Phe Ala Asp Lys Leu His Gln Ala Leu Gln
                245                 250                 255

Glu Thr Glu Pro Asn Tyr Gln Val Leu Ile Arg Ile Leu Ile Ser Arg
            260                 265                 270

Cys Glu Thr Asp Leu Leu Ser Ile Arg Ala Glu Phe Arg Lys Lys Phe
        275                 280                 285

Gly Lys Ser Leu Tyr Ser Ser Leu Gln Asp Ala Val Lys Gly Asp Cys
    290                 295                 300

Gln Ser Ala Leu Leu Ala Leu Cys Arg Ala Glu Asp Met
305                 310                 315
```

<210> SEQ ID NO 11
<211> LENGTH: 321
<212> TYPE: PRT
<213> ORGANISM: Homo sapiens

<400> SEQUENCE: 11

Gly Asp Tyr Val Gln Gly Thr Ile Phe Pro Ala Pro Asn Phe Asn Pro
1               5                   10                  15

Ile Met Asp Ala Gln Met Leu Gly Gly Ala Leu Gln Gly Phe Asp Cys
            20                  25                  30

Asp Lys Asp Met Leu Ile Asn Ile Leu Thr Gln Arg Cys Asn Ala Gln
        35                  40                  45

Arg Met Met Ile Ala Glu Ala Tyr Gln Ser Met Tyr Gly Arg Asp Leu
    50                  55                  60

Ile Gly Asp Leu Arg Glu Gln Leu Ser Asp His Phe Lys Asp Val Met
65                  70                  75                  80

Ala Gly Leu Met Tyr Pro Pro Pro Leu Tyr Asp Ala His Glu Leu Trp
                85                  90                  95

His Ala Met Lys Gly Val Gly Thr Asp Glu Asn Cys Leu Ile Glu Ile
            100                 105                 110

Leu Ala Ser Arg Thr Asn Gly Glu Ile Phe Gln Met Arg Glu Ala Tyr
        115                 120                 125

Cys Leu Gln Tyr Ser Asn Asn Leu Gln Glu Asp Ile Tyr Ser Glu Thr
    130                 135                 140

Ser Gly His Phe Arg Asp Thr Leu Met Asn Leu Val Gln Gly Thr Arg
145                 150                 155                 160

Glu Glu Gly Tyr Thr Asp Pro Ala Met Ala Ala Gln Asp Ala Met Val
                165                 170                 175

Leu Trp Glu Ala Cys Gln Gln Lys Thr Gly Glu His Lys Thr Met Leu
            180                 185                 190

Gln Met Ile Leu Cys Asn Lys Ser Tyr Gln Gln Leu Arg Leu Val Phe
        195                 200                 205

Gln Glu Phe Gln Asn Ile Ser Gly Gln Asp Met Val Asp Ala Ile Asn
    210                 215                 220

Glu Cys Tyr Asp Gly Tyr Phe Gln Glu Leu Leu Val Ala Ile Val Leu
225                 230                 235                 240

Cys Val Arg Asp Lys Pro Ala Tyr Phe Ala Tyr Arg Leu Tyr Ser Ala
                245                 250                 255

Ile His Asp Phe Gly Phe His Asn Lys Thr Val Ile Arg Ile Leu Ile
            260                 265                 270

Ala Arg Ser Glu Ile Asp Leu Leu Thr Ile Arg Lys Arg Tyr Lys Glu
        275                 280                 285

Arg Tyr Gly Lys Ser Leu Phe His Asp Ile Arg Asn Phe Ala Ser Gly
    290                 295                 300

His Tyr Lys Lys Ala Leu Leu Ala Ile Cys Ala Gly Asp Ala Glu Asp
305                 310                 315                 320

Tyr

<210> SEQ ID NO 12
<211> LENGTH: 319
<212> TYPE: PRT
<213> ORGANISM: Homo sapiens

<400> SEQUENCE: 12

Gln Phe Gly Ser Arg Gly Thr Ile Thr Asp Ala Pro Gly Phe Asp Pro
1               5                   10                  15

-continued

Leu Arg Asp Ala Glu Val Leu Arg Lys Ala Met Lys Gly Phe Gly Thr
            20                  25                  30

Asp Glu Gln Ala Ile Ile Asp Cys Leu Gly Ser Arg Ser Asn Lys Gln
        35                  40                  45

Arg Gln Gln Ile Leu Leu Ser Phe Lys Thr Ala Tyr Gly Lys Asp Leu
    50                  55                  60

Ile Lys Asp Leu Lys Ser Glu Leu Ser Gly Asn Phe Glu Lys Thr Ile
65                  70                  75                  80

Leu Ala Leu Met Lys Thr Pro Val Leu Phe Asp Ile Tyr Glu Ile Lys
                85                  90                  95

Glu Ala Ile Lys Gly Val Gly Thr Asp Glu Ala Cys Leu Ile Glu Ile
            100                 105                 110

Leu Ala Ser Arg Ser Asn Glu His Ile Arg Glu Leu Asn Arg Ala Tyr
        115                 120                 125

Lys Ala Glu Phe Lys Lys Thr Leu Glu Glu Ala Ile Arg Ser Asp Thr
    130                 135                 140

Ser Gly His Phe Gln Arg Leu Leu Ile Ser Leu Ser Gln Gly Asn Arg
145                 150                 155                 160

Asp Glu Ser Thr Asn Val Asp Met Ser Leu Ala Gln Arg Asp Ala Gln
                165                 170                 175

Glu Leu Tyr Ala Ala Gly Glu Asn Arg Leu Gly Thr Asp Glu Ser Lys
            180                 185                 190

Phe Asn Ala Val Leu Cys Ser Arg Ser Arg Ala His Leu Val Ala Val
        195                 200                 205

Phe Asn Glu Tyr Gln Arg Met Thr Gly Arg Asp Ile Glu Lys Ser Ile
    210                 215                 220

Cys Arg Glu Met Ser Gly Asp Leu Glu Glu Gly Met Leu Ala Val Val
225                 230                 235                 240

Lys Cys Leu Lys Asn Thr Pro Ala Phe Phe Ala Glu Arg Leu Asn Lys
                245                 250                 255

Ala Met Arg Gly Ala Gly Thr Lys Asp Arg Thr Leu Ile Arg Ile Met
            260                 265                 270

Val Ser Arg Ser Glu Thr Asp Leu Leu Asp Ile Arg Ser Glu Tyr Lys
        275                 280                 285

Arg Met Tyr Gly Lys Ser Leu Tyr His Asp Ile Ser Gly Asp Thr Ser
    290                 295                 300

Gly Asp Tyr Arg Lys Ile Leu Leu Lys Ile Cys Gly Gly Asn Asp
305                 310                 315

<210> SEQ ID NO 13
<211> LENGTH: 315
<212> TYPE: PRT
<213> ORGANISM: Homo sapiens

<400> SEQUENCE: 13

Gly Asn Arg His Ala Lys Ala Ser Ser Pro Gln Gly Phe Asp Val Asp
1               5                   10                  15

Arg Asp Ala Lys Lys Leu Asn Lys Ala Cys Lys Gly Met Gly Thr Asn
            20                  25                  30

Glu Ala Ala Ile Ile Glu Ile Leu Ser Gly Arg Thr Ser Asp Glu Arg
        35                  40                  45

Gln Gln Ile Lys Gln Lys Tyr Lys Ala Thr Tyr Gly Lys Glu Leu Glu
    50                  55                  60

Glu Val Leu Lys Ser Glu Leu Ser Gly Asn Phe Glu Lys Thr Ala Leu
65                  70                  75                  80

-continued

```
Ala Leu Leu Asp Arg Pro Ser Glu Tyr Ala Ala Arg Gln Leu Gln Lys
             85                  90                  95
Ala Met Lys Gly Leu Gly Thr Asp Glu Ser Val Leu Ile Glu Phe Leu
            100                 105                 110
Cys Thr Arg Thr Asn Lys Glu Ile Ile Ala Ile Lys Glu Ala Tyr Gln
            115                 120                 125
Arg Leu Phe Asp Arg Ser Leu Glu Ser Asp Val Lys Gly Asp Thr Ser
            130                 135                 140
Gly Asn Leu Lys Lys Ile Leu Val Ser Leu Leu Gln Ala Asn Arg Asn
145                 150                 155                 160
Glu Gly Asp Asp Val Asp Lys Asp Leu Ala Gly Gln Asp Ala Lys Asp
                165                 170                 175
Leu Tyr Asp Ala Gly Glu Gly Arg Trp Gly Thr Asp Glu Leu Ala Phe
            180                 185                 190
Asn Glu Val Leu Ala Lys Arg Ser Tyr Lys Gln Leu Arg Ala Thr Phe
            195                 200                 205
Gln Ala Tyr Gln Ile Leu Ile Gly Lys Asp Ile Glu Glu Ala Ile Glu
            210                 215                 220
Glu Glu Thr Ser Gly Asp Leu Gln Lys Ala Tyr Leu Thr Leu Val Arg
225                 230                 235                 240
Cys Ala Gln Asp Cys Glu Asp Tyr Phe Ala Glu Arg Leu Tyr Lys Ser
                245                 250                 255
Met Lys Gly Ala Gly Thr Asp Glu Glu Thr Leu Ile Arg Ile Val Val
            260                 265                 270
Thr Arg Ala Glu Val Asp Leu Gln Gly Ile Lys Ala Lys Phe Gln Glu
            275                 280                 285
Lys Tyr Gln Lys Ser Leu Ser Asp Met Val Arg Ser Asp Thr Ser Gly
            290                 295                 300
Asp Phe Arg Lys Leu Leu Val Ala Leu His
305                 310                 315
```